(12) United States Patent
Yoo

(10) Patent No.: US 11,640,652 B2
(45) Date of Patent: May 2, 2023

(54) DISCRETE WAVELET TRANSFORM-BASED NOISE REMOVAL APPARATUS FOR REMOVING NOISE FROM IMAGE SIGNAL AND REMOTE MEDICAL DIAGNOSIS SYSTEM INCLUDING THE SAME

(71) Applicant: HEALCERION CO., LTD., Seoul (KR)

(72) Inventor: Jae Chern Yoo, Gyeonggi-do (KR)

(73) Assignee: HEALCERION CO., LTD., Gyeonggi-do (KR)

(*) Notice: Subject to any disclaimer, the term of this patent is extended or adjusted under 35 U.S.C. 154(b) by 634 days.

(21) Appl. No.: 16/665,169

(22) Filed: Oct. 28, 2019

(65) Prior Publication Data
US 2020/0357098 A1 Nov. 12, 2020

(30) Foreign Application Priority Data
May 7, 2019 (KR) .......................... 10-2019-0053287

(51) Int. Cl.
*G06T 5/00* (2006.01)
*G06T 7/33* (2017.01)
(Continued)

(52) U.S. Cl.
CPC ............ *G06T 5/002* (2013.01); *A61B 5/0022* (2013.01); *A61B 5/0077* (2013.01);
(Continued)

(58) Field of Classification Search
CPC .......... G06T 5/002; G06T 5/50; G06T 7/337; G06T 7/0012; G06T 2207/10016;
(Continued)

(56) References Cited

U.S. PATENT DOCUMENTS 10,265,696 B2    4/2019  Yoo
2009/0040386 A1* 2/2009  Ishiga .................... G06T 5/002
                                                        348/607

(Continued)

FOREIGN PATENT DOCUMENTS

EP    2140412 B1    1/2010
JP    H06-319136 A  11/1994

(Continued)

OTHER PUBLICATIONS

Raj et al. "Denoising Medical Images using Undecimated Wavelet Transform", 2011 IEEE Recent Advances in Intelligent Computation Systems, 2011, pp. 483-488 (Year: 2011).*

(Continued)

*Primary Examiner* — Vu Le
*Assistant Examiner* — Julius Chai
(74) *Attorney, Agent, or Firm* — Harness, Dickey & Pierce, P.L.C.

(57) ABSTRACT

A discrete wavelet transform-based noise removal apparatus and a remote medical diagnosis system using the same. The discrete wavelet transform-based noise removal apparatus can effectively remove noise from various medical images including ultrasound images, images indicative of results of biological or chemical reaction on a bio-disc, images obtained by medical devices, and images for telemedicine.

20 Claims, 6 Drawing Sheets

(51) Int. Cl.
  *G06T 7/00* (2017.01)
  *G16H 40/67* (2018.01)
  *G16H 50/20* (2018.01)
  *G16H 80/00* (2018.01)
  *A61B 5/00* (2006.01)
  *A61B 5/024* (2006.01)
  *A61B 5/055* (2006.01)
  *A61B 6/03* (2006.01)
  *A61B 8/00* (2006.01)
  *A61B 6/00* (2006.01)
  *A61B 8/08* (2006.01)
  *G06T 5/50* (2006.01)

(52) U.S. Cl.
  CPC .......... *A61B 5/02427* (2013.01); *A61B 5/055* (2013.01); *A61B 5/7203* (2013.01); *A61B 5/726* (2013.01); *A61B 6/032* (2013.01); *A61B 6/5258* (2013.01); *A61B 8/4472* (2013.01); *A61B 8/5269* (2013.01); *G06T 5/50* (2013.01); *G06T 7/0012* (2013.01); *G06T 7/337* (2017.01); *G16H 40/67* (2018.01); *G16H 50/20* (2018.01); *G16H 80/00* (2018.01); *A61B 2562/08* (2013.01); *G06T 2207/10016* (2013.01); *G06T 2207/20081* (2013.01); *G06T 2207/20084* (2013.01); *G06T 2207/30048* (2013.01)

(58) Field of Classification Search
  CPC . G06T 2207/20081; G06T 2207/20084; G06T 2207/30048; G16H 40/67; G16H 50/20; G16H 80/00; A61B 5/0077; A61B 5/02427; A61B 5/055; A61B 5/7203; A61B 5/726; A61B 6/032; A61B 6/5258; A61B 8/4472; A61B 8/5269; A61B 2562/08
  See application file for complete search history.

(56) References Cited

U.S. PATENT DOCUMENTS

| | | | | |
|---|---|---|---|---|
| 2011/0235925 | A1* | 9/2011 | Itoh | G08B 13/1961 382/218 |
| 2012/0019690 | A1* | 1/2012 | Stirling-Gallacher | G01S 7/2923 348/241 |
| 2013/0216117 | A1* | 8/2013 | Mercuriev | G06T 5/002 382/132 |
| 2015/0325014 | A1* | 11/2015 | Nakagawa | G06T 11/008 382/128 |
| 2015/0375226 | A1 | 12/2015 | Yoo | |
| 2016/0343115 | A1* | 11/2016 | Kusumi | G06T 5/20 |
| 2016/0358314 | A1* | 12/2016 | Ji | H04N 19/36 |
| 2017/0159136 | A1* | 6/2017 | Church | C12Q 1/6841 |

FOREIGN PATENT DOCUMENTS

| | | |
|---|---|---|
| JP | 2009-219066 A | 9/2009 |
| JP | 2010-239296 A | 10/2010 |
| JP | 2017-015724 A | 1/2017 |
| JP | 2018-192247 A | 12/2018 |
| KR | 10-2010-0014065 A | 2/2010 |
| KR | 10-2010-0020424 A | 2/2010 |
| KR | 10-1959438 B1 | 3/2019 |
| KR | 10-2019-0074733 A | 6/2019 |

OTHER PUBLICATIONS

X. Zhou, C. Zhou and B. G. Stewart, "Comparisons of discrete wavelet transform, wavelet packet transform and stationary wavelet transform in denoising PD measurement data," Conference Record of the 2006 IEEE International Symposium on Electrical Insulation, 2006, pp. 237-240, doi: 10.1109/ELINSL.2006 (Year: 2006).*

J. Madhura, Y. Amith, A. Gurjar, K. Ayappa, M. Bharath and M. L. Goutham, "Methods of impulsive noise reduction using image processing," 2017 International conference of Electronics, Communication and Aerospace Technology (ICECA), 2017, pp. 296-302, doi: 10.1109/ICECA.2017.8203691. (Year: 2017).*

G. Cincotti, G. Loi and M. Pappalardo, "Frequency decomposition and compounding of ultrasound medical images with wavelet packets," in IEEE Transactions on Medical Imaging, vol. 20, No. 8, pp. 764-771, Aug. 2001, doi: 10.1109/42.938244. (Year: 2001).*

N. Mustafa, S. A. Khan, J. -P. Li, M. Khalil, K. Kumar and G. Mohaned, "Medical image De-noising schemes using wavelet transform with fixed form thresholding," 2014 11th International Computer Conference on Wavelet Actiev Media Technology and Information Processing(ICCWAMTIP), 2014, pp. 397-402, doi: (Year: 2014).*

Office Action from corresponding Korean Patent Application No. 10-2019-0053287, dated Apr. 9, 2020.

* cited by examiner

DISCRETE WAVELET TRANSFORM-BASED NOISE REMOVAL APPARATUS FOR REMOVING NOISE FROM IMAGE SIGNAL AND REMOTE MEDICAL DIAGNOSIS SYSTEM INCLUDING THE SAME

CROSS-REFERENCE TO RELATED APPLICATION

This application claims the benefit of and priority to Korean Patent Application 10-2019-0053287, filed on May 7, 2019, the entire disclosure of which is incorporated herein by reference.

FIELD

The present invention relates to a discrete wavelet transform-based noise removal apparatus for effectively removing noise from various medical images including ultrasound images, images indicative of results of biological or chemical reaction on a bio-disc, images obtained by medical devices, and images for telemedicine, a remote medical diagnosis system using the same, and a remote medical diagnosis method using the same.

More particularly, the present invention relates to a noise removal apparatus for removing noise from an image, which divides a noisy image into a high-frequency image containing a lot of noise and a low-frequency image containing less noise by discrete wavelet transform, performs summing and averaging of the high-frequency image and plural noise images generated by a noise generator to cancel out noise to obtain a noise-attenuated high-frequency image, and synthesizes the noise-attenuated high-frequency image with the low-frequency image to obtain a denoised image, a remote medical diagnosis system using the same, and a remote medical diagnosis method using the same.

The noise removal apparatus according to the present invention and the remote medical diagnosis system using the same are advantageously used in removing various types of noise including speckle noise appearing in images indicative of results of biological or chemical reaction on a bio-disc or a lap-on-a-disc, ultrasound images, and images for telemedicine, and, in the field of medicine, advantageously used in implementing a virtual doctor that automatically analyzes the state of a patient based on medical images, such as X-ray, ultrasound, CT, and MRI images, using an artificial intelligence neural network (or artificial neural network) and notifies the patient or a doctor of an analysis result.

Particularly, in implementing a virtual doctor using medical images containing a lot of noise, such as ultrasound images, in order to obtain a high-performance AI-based virtual doctor, a given artificial neural network needs to be trained in advance on a large amount of high-quality medical images by deep learning. The discrete wavelet transform-based noise removal apparatus according to the present invention and the remote medical diagnosis system using the same can remove noise from an medical image before training an artificial neural network by deep learning, thereby allowing efficient deep learning and significant improvement in performance of the virtual doctor.

BACKGROUND

This application is a continuation of an earlier-issued European patent titled "Remote Medical-Diagnosis System and Method" (issued on Dec. 12, 2018, patent number: 02140412).

In addition, this application is a continuation of an earlier-filed U.S. patent titled "Nucleic Acid Amplification Disc Device Using Heat-Sensitive Polymer Composite, and Analysis Method Using Same" (application Ser. No. 14/758, 444).

Further, this application is a continuation of an earlier-filed Korean patent "Lab-on-a-disc Device Using Black Thermoplastic Resin Valve and Non-contact temperature sensor" (application number: 10-2017-0176306) and an earlier-filed U.S. patent titled "Thin Film Valve Device Using Fluid Hole Closing Membrane" (application Ser. No. 14/732,664).

The earlier-issued patent discloses a remote medical diagnosis system and a remote medical diagnosis method using the same, wherein the remote medical diagnosis system includes: a bioanalyzer including a bio-disc or a lab-on-a-disc adapted to receive a sample therein to perform a biological, chemical or biochemical reaction; a virtual doctor including a medical examination device including a thermometer, a sphygmomanometer, a camera, a stethoscope, a body fat analyzer, a vascular screening device, an ultrasound imager, a urinalysis device, a pulsimeter, a blood collection device, an electrocardiographer, an X-ray device, an oxygen saturation tester, a dementia testing device, a computerized axial tomographer (CAT), a magnetic resonance imager (MRI), a capsule endoscope, a magnifier, a camera-integrated magnifier, and a bioshirt having a function of measuring biological signals (diabetes, obesity, blood pressure, pulse, electrocardiogram, body temperature, and the like), the virtual doctor residing as software in a user terminal to guide or instruct how to use the bioanalyzer and the medical examination device and to provide a consultation service with a user; the user terminal providing a consultation service with a medical expert or the virtual doctor; a medical expert terminal providing a consultation service with a user; and a remote diagnosis server connecting a user to a medical expert as a consultation specialist during a regular medical check-up period, connecting a user to the virtual doctor during the other periods, and blocking connection between the user and the virtual doctor if the regular medical check-up period elapses without consultation with the medical expert.

In addition, the earlier-filed patents disclose: a nucleic acid amplification disc using a temperature-sensitive polymer composite which can be used in remote medical diagnosis, and an analysis method using the same; and a porous thin-film valve device controlling a flow of fluid on the nucleic acid amplification disc and a bio-disc.

Recently, image processing technology provides us with high-quality image data in modern life. In particular, such image processing technology is used in improving quality of various images, such as digital camera images, images indicative of results of bioreaction on a bio-disc, images for telemedicine, space exploration images, and ultrasound medical images. However, image data such as images indicative of results of bioreaction on a bio-disc, images for telemedicine, space exploration images, and ultrasound medical images contains not only a desired image signal but also lots of various noise components, causing difficulty in acquiring high-quality images. Recently, various image processing methods have been studied to reduce noise to improve image quality.

In general, various types of noise, including speckle noise, are generated due to the surrounding environment or channel interference in the process of acquiring or transmitting an image. However, noise in images for telemedicine, space exploration images, and medical image data is not easily removed by general noise reduction algorithms. Further, even when such noise is removed, high-frequency band data in image signals is often severely damaged, causing difficulty in accurate interpretation of the images by non-professionals. Such noise reduction algorithms may be divided into an algorithm using the concept of restoration and an algorithm using filtering techniques, such as a median filter and a Weiner filter. Since accurate modeling of noise is a prerequisite for the restoration-based algorithm, the restoration-based algorithm has difficulty in noise removal in real situations where accurate modeling of noise is difficult.

On the other hand, the algorithm using filtering techniques removes not only noise but also a high-frequency component essential to an image, thus causing removal of details of the image, which results in a phenomenon of damage to a high-frequency region such as an edge component, called "blurring".

Since a high-frequency component of an image contains a component representing a boundary of an object in the image along with a noise component, if noise is removed by suppressing the high-frequency component as in typical methods, characteristics of an original signal can also be reduced along with undesirable noise, causing blurring. Therefore, there is a need for a method that can effectively remove noise from an image while preserving characteristics of the image.

In particular, ultrasound images, a representative example of medical images, are often damaged by speckle noise generated due to interference between ultrasound signals and thus have poor quality, making it difficult even for a medical expert to recognize and analyze the images. Therefore, it is necessary to acquire images useful for diagnosis by reducing speckle noise in an ultrasound image.

SUMMARY

Embodiments of the present invention have been conceived to solve such problems in the art and aspects of the present invention provide a discrete wavelet transform-based noise removal apparatus which can effectively remove noise from an image while preserving details of the image containing useful information, a remote medical diagnosis system using the same, and a remote medical diagnosis method using the same, wherein the noise removal apparatus divides a noisy image into a high-frequency image and a low-frequency image by discrete wavelet transform, performs summing and averaging of the high-frequency image and plural noise images generated by a noise generator to cancel out noise to obtain a noise-attenuated high-frequency image, and synthesizes the noise-attenuated high-frequency image with the low-frequency image to obtain a denoised image.

Other aspects of the present invention provide a discrete wavelet transform-based noise removal apparatus which further includes an AI neural network (or artificial neural network) trained on an image database accumulated by a medical device, such as X-ray, ultrasound, CT, and MRI devices, by deep learning to automatically analyze the state of a patient, a remote medical diagnosis system using the same, and a remote medical diagnosis method using the same.

However, it should be understood that the technical problem to be solved by embodiments of the present invention is not limited to the aforementioned technical problems and other technical problems may exist.

In accordance with one aspect of the present invention, a noise removal apparatus includes: an image signal reception sensor unit receiving a measured image signal; a wavelet transform unit performing discrete wavelet transform on the image signal received from the image signal reception sensor unit to divide the image signal into a low-frequency image composed of a low-frequency component and a high-frequency image composed of a high-frequency component; a noise generator generating plural noise images containing noise similar to a noise component in the high-frequency image; a high-frequency image summation unit summing and averaging the high-frequency image and the plural noise images generated by the noise generator to generate a noise-attenuated high-frequency image; and an inverse discrete wavelet transform unit synthesizing the low-frequency image and the noise-attenuated high-frequency image to generate a denoised image.

In accordance with another aspect of the present invention, a noise removal apparatus includes: an image signal reception sensor unit receiving a measured video; a wavelet transform unit performing discrete wavelet transform on images in the original video received from the image signal reception sensor unit and composed of plural consecutive frames to divide each of the images into a low-frequency video image composed of a low-frequency component and a high-frequency video image composed of a high-frequency component; a high-frequency video image summation unit summing and averaging the high-frequency video images obtained from the original video composed of the plural consecutive frames to generate a noise-attenuated high-frequency image; and an inverse discrete wavelet transform unit synthesizing the noise-attenuated high-frequency image with a low-frequency image corresponding to a middle frame among the low-frequency video images to generate a denoised image.

The low-frequency image or the low-frequency video image may include a sub-band LL image, a sub-band HL image, and a sub-band LH image, and the high-frequency image or the high-frequency video image may include a sub-band HH image.

The high-frequency image may include a high-frequency sub-band image obtained by performing discrete wavelet transform or discrete wavelet packet transform with two or more decomposition levels.

The noise removal apparatus according to the present invention may further include: a silence detector determining the presence of an input signal from the image signal reception sensor unit; a threshold generation unit generating a threshold for distinguishing noise in the sub-band HH image from actual image data; and an HH thresholder regarding a pixel in the sub-band HH image having a smaller value than the threshold as a noise pixel and interpolating the noise pixel using neighboring pixels without interpolation of a pixel in the sub-band HH image having a greater value than the threshold to generate a noise-free sub-band HH image.

The noise removal apparatus according to the present invention may further include: a logarithmic transform unit logarithmically transforming the sub-band HH images to remove speckle noise; and an exponential transform unit inversely transforming the logarithmically transformed sub-band HH image back into an original form thereof.

The noise removal apparatus according to the present invention may further include: a speckle noise removal command unit determining whether to remove speckle noise; a logarithmic transform selection switch; and an exponential transform selection switch, wherein the logarithmic transform selection switch and the exponential transform selection switch may be activated or deactivated by the speckle noise removal command unit.

The noise removal apparatus according to the present invention may further include a heart pulse sensor, wherein the image signal reception sensor unit may receive an image signal or a video synchronized with a heart pulse signal.

The noise removal apparatus according to the present invention may further include: an image aligner performing registration or alignment between the frames of the original video; and an outlier detection unit detecting a matching image containing feature points at which a motion vector between a reference image and the matching image exceeds a predetermined value upon registration between the frames by the image aligner to exclude the matching image from the summing and averaging process performed by the high-frequency video image summation unit.

The image aligner may perform alignment or registration between two neighboring frames using semantic segmentation-based image registration, control point mapping-based image registration, or wavelet frame-based image matching.

In accordance with a further aspect of the present invention, a remote medical diagnosis system includes: a bioanalyzer; a user terminal; and a medical expert terminal, wherein: the bioanalyzer includes a bio-disc performing a biological, chemical or biochemical reaction, a central controller driving the bio-disc, the noise removal apparatus according to the present invention, and an image sensor capturing a result of bioreaction performed on the bio-disc as image data; a user terminal including a camera monitoring use of the bioanalyzer, a first authentication unit authenticating a product ID of the bio-disc, a recording unit storing denoised image data obtained by removing noise from the captured image data using the noise removal apparatus, an Internet connector transmitting the denoised image data and the product ID of the bio-disc to a remote diagnosis server via a communication network and providing a communication channel for a remote consultation service, a first consultation service unit providing a consultation service with a medical expert, an artificial neural network residing as software therein and trained on an image database accumulated by the bioanalyzer by deep learning, and a virtual doctor residing as software therein and comprising a guide unit guiding how to use the bioanalyzer or instructing to use the bioanalyzer and a diagnosis unit outputting a diagnostic result obtained by automatic analysis of the denoised image data obtained by the noise removal apparatus using the deep learning-trained artificial neural network, the user terminal being connected to the noise removal apparatus via a communication interface; and the medical expert terminal includes a receiver receiving the image data via the communication network and a second consultation service unit providing a consultation service between a user and a medical expert.

In accordance with yet another aspect of the present invention, a remote medical diagnosis system includes: a medical device; the noise removal apparatus according to the present invention; a user terminal; and a medical expert terminal, wherein: the medical device performs X-ray examination, ultrasound examination, CT examination, or MRI examination and includes a wireless transmitter wirelessly transmitting medical image data on a patient measured by the medical device; the user terminal includes a camera monitoring use of the medical device, a second authentication unit wirelessly authenticating a product ID of the medical device, a recording unit storing denoised medical image data on the patient, the denoised medical image data being obtained by removing noise from the image data on the patient received from the wireless transmitter using the noise removal apparatus, an Internet connector transmitting the denoised medical image data on the patient and the product ID of the medical device to a remote diagnosis server via a communication network and providing a communication channel for a remote consultation service, a third consultation service unit providing a consultation service with a medical expert, an artificial neural network residing as software therein and trained on a medical image database accumulated by the medical device by deep learning, and a virtual doctor residing as software therein and comprising a guide unit guiding how to use the medical device or instructing to use the medical device and a diagnosis unit outputting a diagnostic result obtained by automatic analysis of the denoised medical image data obtained by the noise removal apparatus using the deep learning-trained artificial neural network, the user terminal being connected to the noise removal apparatus via a communication interface; and the medical expert terminal includes a receiver receiving the medical image data via the communication network and a fourth consultation service unit providing a consultation service between a user and a medical expert.

In accordance with yet another aspect of the present invention, a remote medical diagnosis method includes the steps of: removing, by the noise removal apparatus according to the present invention, noise from medical image data on a patient obtained by a medical device; training an artificial neural network on a database accumulated by the medical device by deep learning; outputting a diagnostic result obtained by automatic analysis of the denoised medical image data obtained by the noise removal apparatus using the deep learning-trained artificial neural network; and transmitting the denoised medical image data to a remote diagnosis server via a communication network and providing a remote consultation service with a medical expert.

In accordance with yet another aspect of the present invention, a noise removal apparatus includes: an image signal reception sensor unit receiving a measured image signal; a wavelet transform unit performing discrete wavelet transform on the received image signal to divide the image signal into a low-frequency image composed of a low-frequency component and a high-frequency image composed of a high-frequency component; a noise generator generating plural noise images containing noise similar to a noise component in the high-frequency image; a high-frequency image summation unit generating a noise-attenuated high-frequency image based on the high-frequency image and the noise images; and an inverse discrete wavelet transform unit synthesizing the low-frequency image and the noise-attenuated high-frequency image to generate a denoised image.

The wavelet transform unit may decompose the original image into four sub-band images including an LL image, an HL image, an LH image, and an HH image by performing discrete wavelet transform.

The low-frequency image may include a sub-band LL image, a sub-band HL image, and a sub-band LH image, and the high-frequency image may include a sub-band HH image.

The wavelet transform unit may perform discrete wavelet transform with two or more decomposition levels, wherein the high-frequency image may include a sub-band HHHH image.

The noise removal apparatus may further include: a silence detector determining the presence of an input signal from the image signal reception sensor unit; a threshold generation unit generating a threshold for distinguishing noise in the noise-attenuated high-frequency image obtained by the high-frequency image summation unit from actual image data when the silence detector detects the absence of the input signal; and a threshold determination unit comparing the generated threshold with a pixel value in the noise-attenuated high-frequency image to remove noise from the noise-attenuated high-frequency image.

The noise removal apparatus may further include: a logarithmic transform unit transforming the high-frequency image obtained by discrete wavelet transform into logarithmic form; an exponential transform unit transforming the noise-attenuated high-frequency image generated by the high-frequency image summation unit into exponential form; and a multiplicative noise removal command unit controlling whether to activate the logarithmic transform unit and the exponential transform unit.

The received image signal may be synchronized with a heart pulse signal measured by a heart pulse sensor.

In accordance with yet another aspect of the present invention, a noise removal apparatus includes: an image signal reception sensor unit receiving a measured video composed of plural video images; a wavelet transform unit performing discrete wavelet transform on the plural video images in the received video to divide each of the plural video images into a low-frequency video image composed of a low-frequency component and a high-frequency video image composed of a high-frequency component; a high-frequency video image summation unit generating a noise-attenuated high-frequency image based on the high-frequency video images; and an inverse discrete wavelet transform unit synthesizing the noise-attenuated high-frequency video image with the low-frequency video image obtained from any one of the plural video images to generate a denoised image.

The inverse discrete wavelet transform unit may generate the denoised image by synthesizing the noise-attenuated high-frequency video image with the low-frequency video image obtained from a middle video image among the plural video images.

The wavelet transform unit may decompose each of the plural video images into four sub-band images including an LL image, an HL image, an LH image, and an HH image by performing discrete wavelet transform.

The low-frequency video image may include a sub-band LL image, a sub-band HL image, and a sub-band LH image, and the high-frequency video image may include a sub-band HH image.

The low-frequency video image may include a sub-band LL image, a sub-band HL image, and a sub-band LH image, and the high-frequency video image may include a sub-band HH image.

The noise removal apparatus may further include: a silence detector determining the presence of an input signal from the image signal reception sensor unit; a threshold generation unit generating a threshold for distinguishing noise in the noise-attenuated high-frequency video image obtained by the high-frequency video image summation unit from actual image data when the silence detector detects the absence of the input signal; and a threshold determination unit comparing the generated threshold with a pixel value in the noise-attenuated high-frequency video image to remove noise from the noise-attenuated high-frequency video image.

The noise removal apparatus may further include: a logarithmic transform unit transforming each of the high-frequency video images obtained by discrete wavelet transform into logarithmic form; an exponential transform unit transforming the noise-attenuated high-frequency video image generated by the high-frequency video image summation unit into exponential form; and a multiplicative noise removal command unit controlling whether to activate the logarithmic transform unit and the exponential transform unit.

The noise removal apparatus may further include: an image aligner performing registration between the received plural video images; and an outlier detection unit eliminating a matching image significantly misaligned with a reference image upon registration between the video images by the image aligner.

The image aligner may perform registration between the video images using semantic segmentation-based image registration, control point mapping-based image registration, or wavelet frame-based image registration.

In accordance with yet another aspect of the present invention, a noise removal method includes the steps of: (a) receiving a measured image signal; (b) dividing the received image signal into a low-frequency image composed of a low-frequency component and a high-frequency image composed of a high-frequency component by performing discrete wavelet transform; (c) generating plural noise images containing noise similar to a noise component in the high-frequency image; (d) generating a noise-attenuated high-frequency image based on the high-frequency image and the noise images; and (e) generating a denoised image by synthesizing the low-frequency image with the noise-attenuated high-frequency image by performing inverse discrete wavelet transform.

In step (b), the original image may be decomposed into four sub-band images including an LL image, an HL image, an LH image and an HH image by discrete wavelet transform.

The low-frequency image may include a sub-band LL image, a sub-band HL image, and a sub-band LH image, and the high-frequency image may include a sub-band HH image.

In step (b), discrete wavelet transform with two or more decomposition levels may be performed, wherein the high-frequency image may include a sub-band HHHH image.

The noise removal method may further include the steps of: (f) determining the presence of an input signal in step (a); (g) generating a threshold for distinguishing noise in the noise-attenuated high-frequency image obtained by the high-frequency image summation unit from actual image data upon determining that there is no input signal; and (h) removing noise from the noise-attenuated high-frequency image by comparing the generated threshold with a pixel value in the noise-attenuated high-frequency image.

The noise removal method may further include the steps of: (i) transforming the high-frequency image obtained by wavelet transform into logarithmic form when there is multiplicative noise in the received image signal; and (j) transforming the noise-attenuated high-frequency image generated by the high-frequency image summation unit into exponential form.

In accordance with yet another aspect of the present invention, a noise removal method includes the steps of: (a) receiving a measured video composed of plural video images; (b) dividing each of the plural video images in the received video into a low-frequency video image composed of a low-frequency component and a high-frequency video image composed of a high-frequency component by performing discrete wavelet transform; (c) generating a noise-attenuated high-frequency video image based on the high-frequency video images; and (d) generating a denoised image by synthesizing the noise-attenuated high-frequency video image with the low-frequency video image obtained from any one of the plural video images by inverse discrete wavelet transform.

In step (d), the denoised image may be generated by synthesizing the noise-attenuated high-frequency video image with the low-frequency video image obtained from a middle video image among the plural video images.

In step (b), each of the plural video images may be decomposed into four sub-band images including an LL image, an HL image, an LH image, and an HH image by performing discrete wavelet transform.

The low-frequency video image may include a sub-band LL image, a sub-band HL image, and a sub-band LH image, and the high-frequency video image may include a sub-band HH image.

In step (b), discrete wavelet transform with two or more decomposition levels may be performed, wherein the high-frequency image may include a sub-band HHHH image.

The noise removal method may further include the steps of: (e) determining the presence of an input signal in step (a); (f) generating a threshold for distinguishing noise in the noise-attenuated high-frequency video image obtained by the high-frequency video image summation unit from actual image data upon determining that there is no input signal; and (g) removing noise from the noise-attenuated high-frequency video image by comparing the generated threshold with a pixel value in the noise-attenuated high-frequency video image.

The noise removal method may further include the steps of: (h) transforming each of the high-frequency video images obtained by discrete wavelet conversion into logarithmic form when there is a multiplicative noise in the received plural video images; and (i) transforming the noise-attenuated high-frequency video image generated by the high-frequency video image summation unit into exponential form.

The noise removal method may further include the steps of: (j) performing registration between the received plural video images; and (k) removing a matching image significantly misaligned with a reference image upon registration between the received plural video images.

Registration between the received plural video images may be performed by semantic segmentation-based image registration, control point mapping-based image registration, or wavelet frame-based image registration.

In accordance with yet another aspect of the present invention, a remote medical diagnosis system includes: the noise removal apparatus according to any one of the above embodiments; a user terminal connected to the noise removal apparatus via a communication interface and providing a user with a consultation service with a medical expert using a denoised image; a remote diagnosis server transmitting data between the user terminal and a medical expert terminal; and the medical expert terminal receiving image data from the remote diagnosis server and providing a user with a consultation service with a medical expert.

The user terminal may include a recording unit storing denoised image data or denoised video data received from the noise removal apparatus; a first authentication unit authenticating a product ID of an image signal measurement device; a camera monitoring use of the image signal measurement device; an artificial neural network trained on an image database or video database accumulated by the image signal measurement product by deep learning; a guide unit residing as software therein and guiding how to use the image signal measurement device; a diagnostic unit outputting a diagnostic result obtained by automatic analysis of the image data or video data obtained by the noise removal apparatus using the deep learning-trained artificial neural network; an Internet connector transmitting the denoised image data or denoised video data and the product ID to the remote diagnosis server via a communication network and providing a communication channel for a remote consultation service; and a first consultation service unit providing a consultation service between a user and a medical expert. The medical expert terminal may include: a receiver receiving the denoised image data or denoised video data via the communication network; and a second consultation service unit providing a consultation service between a user and a medical expert.

It should be understood that the aforementioned solutions are provided for illustration only and are not to be construed in any way as limiting the present invention. In addition to the exemplary embodiments described above, other embodiments may exist in the drawings and detailed description of the invention.

The present invention provides a discrete wavelet transform-based noise removal apparatus which can effectively remove noise from various medical images including ultrasound images, image data on results of biological or chemical reaction on a bio-disc, images obtained by a medical device, and images for telemedicine, and a remote medical diagnosis system using the same.

However, it should be understood that the effects obtainable by the present invention are not limited to the aforementioned effects and other effects may exist.

BRIEF DESCRIPTION OF THE DRAWINGS

FIG. 1 is a schematic block diagram of a discrete wavelet transform-based noise removal apparatus for removing noise from one image. FIG. 1 is a schematic block diagram of a discrete wavelet transform-based noise removal apparatus for removing noise from a video composed of plural video images.

DETAILED DESCRIPTION

Figure 1:
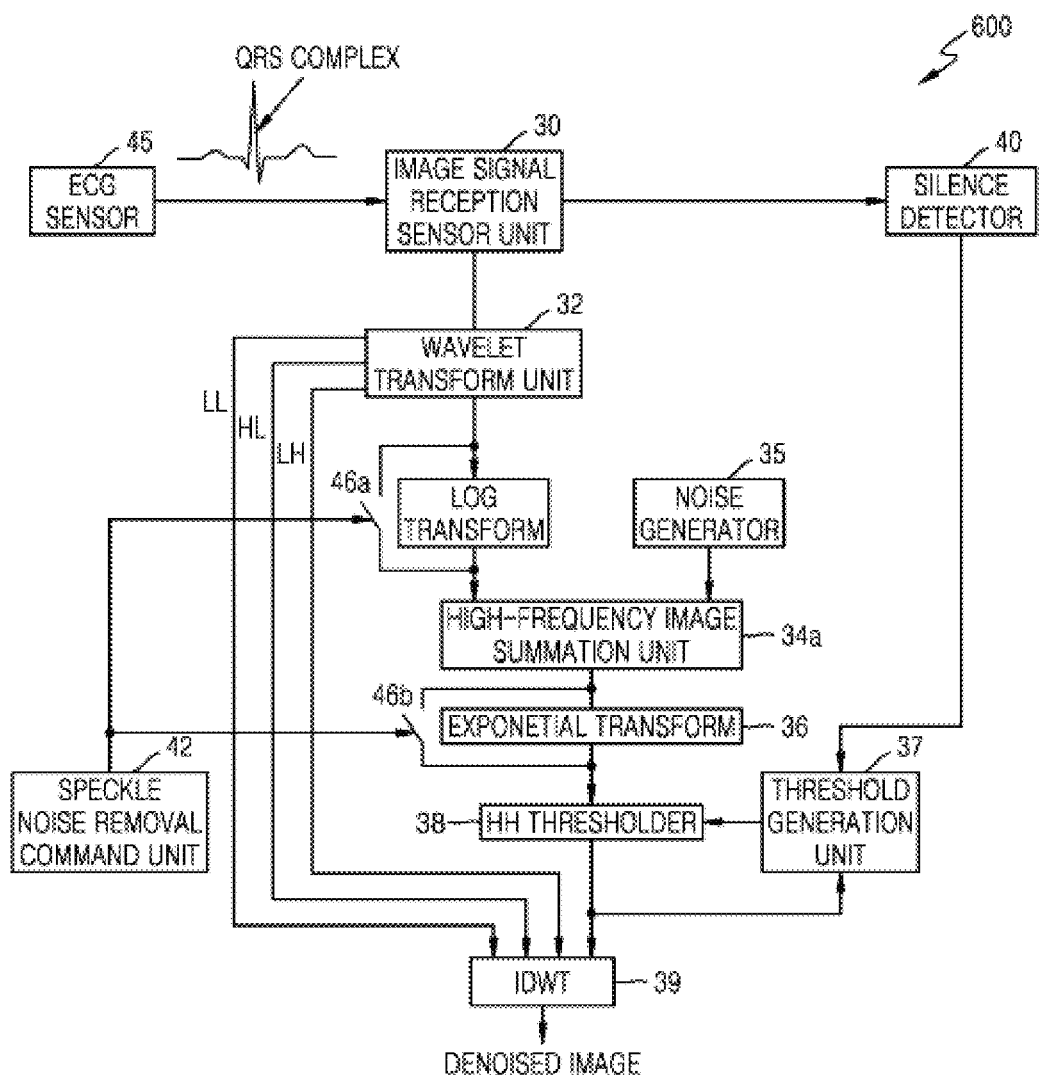
FIG. 1 and FIG. 2 show various embodiment of a discrete wavelet transform-based noise removal apparatus for removing noise from image signals.

Now, exemplary embodiments of the present invention will be described in detail with reference to the accompanying drawings so that those skilled in the art can easily implement the present invention. It should be understood that the present invention is not limited to the following embodiments and may be embodied in different ways. In the drawings, portions irrelevant to the description will be omitted for clarity. Like components will be denoted by like reference numerals throughout the specification.

It will be understood that, when an element is referred to as being "connected to" another element, it can be directly connected to the other element, or can be electrically or indirectly connected to the other element with a different element interposed therebetween.

It will be understood that when an element is referred to as being "on," "above," "at an upper end of," "under," "below," "at a lower end of" another element, it may directly adjoin the other element or layer, or intervening elements may be present.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups.

Hereinafter, exemplary embodiments of the present invention will be described in detail with reference to the accompanying drawings.

FIG. 1 is a block diagram of a discrete wavelet transform-based noise removal apparatus 600 for removing noise from image signals according to one embodiment of the present invention. The noise removal apparatus 600 according to this embodiment may include: an image signal reception sensor unit 30 receiving an image signal from an image sensor, an ultrasound array sensor, or a medical sensor; a wavelet transform unit 32 performing discrete wavelet transform on an original 2D image received from the image signal reception sensor unit 30 to decompose the original 2D image into four sub-band images, that is, a sub-band LL image, a sub-band LH image, a sub-band HL image, and a sub-band HH image; a noise generator 35 generating plural noise images containing noise similar to a noise component in the sub-band HH image; a high-frequency image summation unit 34a summing and averaging the sub-band HH image and the plural noise images generated by the noise generator 35 to cancel out noise in the sub-band HH image to obtain a noise-attenuated sub-band HH image; and an inverse discrete wavelet transform (IDWT) unit 39 synthesizing the noise-attenuated sub-band HH image with the sub-band LL image, the sub-band LH image, and the sub-band HL image. As used herein, the term "noise image containing noise similar to a noise component in the sub-band HH image" may refer to, for example, an image containing a noise component that is within a predetermined margin of error relative to a noise component in a high-frequency image in terms of at least one selected from the group of size, frequency, pixel amount, and pixel RGB value.

The image signal reception sensor unit 30 may receive a measured image signal. The wavelet transform unit 32 may perform discrete wavelet transform on the received image signal to divide the received image signal into a low-frequency image composed of a low-frequency component and a high-frequency image composed of a high-frequency component. The noise generator 35 may generate the plural noise images containing noise similar to the noise component in the high-frequency image. The high-frequency image summation unit 34a may generate a noise-attenuated high-frequency image based on the high-frequency image and the noise images. The inverse discrete wavelet transform unit 39 may generate a denoised image by synthesizing the low-frequency image with the noise-attenuated high-frequency image.

In the present invention, the wavelet transform unit 32 may decompose the original image into four sub-band images including an LL image, an HL image, an LH image and an HH image by performing discrete wavelet transform. Here, discrete wavelet transform by the wavelet transform unit 32 may be applying a low pass filter and a high pass filter in a horizontal or vertical direction of the 2D image, followed by downsampling by a factor of 2 to decompose the 2D image into four sub-band images, that is, the sub-band LL image, the sub-band HL image, the sub-band LH image and the sub-band HH image.

Here, the sub-band LL image is obtained by applying the low pass filter in both horizontal and vertical directions of the original image, followed by subsampling by a factor of ½ in each of the horizontal and vertical directions. The sub-band HL image is obtained by applying the low pass filter and the high pass filter in the horizontal and vertical directions of the original ultrasound image, respectively, followed by subsampling by a factor of ½ in each of the horizontal and vertical directions. The sub-band LH image is obtained by applying the high pass filter and the low pass filter in the horizontal and vertical directions of the original ultrasound image, respectively, followed by subsampling by a factor of ½ in each of the horizontal and vertical directions. The sub-band HH image is obtained by applying the high pass filter in both the horizontal and vertical directions of the original ultrasound image, followed by subsampling by a factor of ½ in each of the horizontal and vertical directions.

In the present invention, the low-frequency image may include the sub-band LL image, the sub-band HL image, and the sub-band LH image and the high-frequency image may include the sub-band HH image.

If the wavelet transform unit 32 performs discrete wavelet packet transform with one decomposition level, the original image is decomposed into four sub-band LL images, that is, an LL image, an LH image, an HL image, and an HH image. In addition, if the wavelet transform unit 32 performs discrete wavelet packet conversion again with respect to the four sub-band images, 16 sub-band images, that is, LLLL, LLLH, LLHL, LLHH, LHLL, LHLH, LHHL, LHHH, HLLL, HLLH, HLHL, HLHH, HHLL, HHLH, HHHL, HHHH images, are obtained.

In another embodiment, the wavelet transform unit 32 may perform discrete wavelet transform with two or more decomposition levels, wherein the high-frequency image may include a sub-band HHHH image. Preferably, the high-frequency image is a sub-band HHHH image obtained by performing discrete wavelet packet transform with two decomposition levels or a high-frequency sub-band image obtained by performing discrete wavelet packet transform with two or more decomposition levels.

The noise generator 35 generates the plural noise images containing noise similar to the noise component in the high-frequency image. The noise generator 35 generates random numbers following a distribution having a predetermined average and variance to generate the plural noise images. The high-frequency image summation unit 34a generates the noise-attenuated high-frequency image based on the high-frequency image and the noise images.

In the present invention, the high-frequency image summation unit 34a may obtain the noise-attenuated high-frequency image by summing and averaging the high-frequency image and the plural noise images. Herein, summing and averaging by the high-frequency image summation unit 34a may be summing plural 2D images into one 2D image, followed by dividing pixel-by-pixel values of the one 2D image by the total number of summed images to obtain one final 2D image.

In FIG. 1, an average and variance of noise generated by the noise generator 35 is preferably set such that an average power of the image obtained by summing and averaging the sub-band HH image and the plural noise images generated by the noise generator 35 using the high-frequency image summation unit 34a is minimized or is equal to a DC value (average value) of the sub-band LL image when there is no input signal from the image signal reception sensor unit 30.

Since the ideal average and variance of the noise are set assuming that there is no input signal, the average power of the image obtained by the high-frequency image summation unit 34a is equal to 0 or the DC value (average value) of the sub-band LL image.

The inverse discrete wavelet transform unit 39 may generate the denoised image by synthesizing the low-frequency image with the noise-attenuated high-frequency image. In the present invention, the low-frequency image may mean the sub-band LL image, the sub-band LH image, and the sub-band HL image, wherein the inverse discrete wavelet transform unit 39 may synthesize the noise-attenuated sub-band HH image with the sub-band LL image, the sub-band LH image, and the sub-band HL image.

Figure 2:
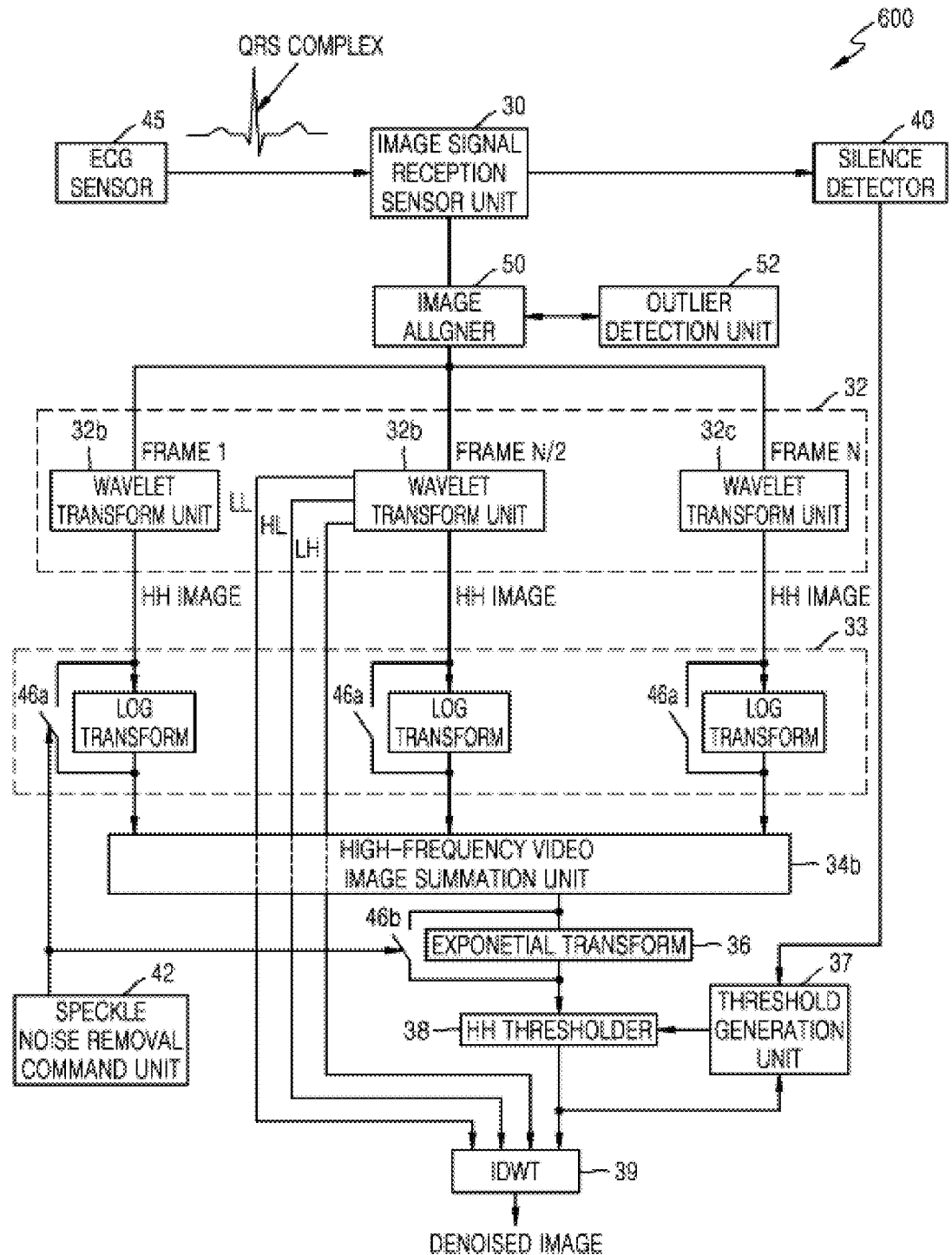

FIG. 2 is a block diagram of a discrete wavelet transform-based noise removal apparatus 600 for removing noise from image signals according to another embodiment of the present invention. The noise removal apparatus 600 according to this embodiment may include: an image signal reception sensor unit 30 receiving a video signal from an image sensor, an ultrasound array sensor, or a medical sensor; a wavelet transform unit 32 performing discrete wavelet transform on the original 2D video received from the image signal reception sensor unit 30 and composed of n consecutive frames (n video images) to decompose the video image into four sub-band images, that is, a sub-band LL image, a sub-band LH image, a sub-band HL image, and a sub-band HH image; a high-frequency video image summation unit 34b summing and averaging the sub-band HH images obtained from the original 2D video composed of n frames to cancel out noise in the sub-band HH image to obtain a noise-attenuated sub-band HH image; and an inverse discrete wavelet transform unit 39 synthesizing the noise-attenuated sub-band HH image with the sub-band LL image, the sub-band LH image, and the sub-band HL image.

As used herein, the term "frame" may refer to a single video image. Preferably, the original video is composed of 100 or less 5 s or less long consecutive frames.

The image signal reception sensor unit 30 may receive a measured video composed of plural video images. The wavelet transform unit 32 may perform discrete wavelet transform on the plural video images in the received video to divide each of the plural video images into a low-frequency video image composed of a low-frequency component and a high-frequency video image composed of a high-frequency component.

In the present invention, the wavelet transform unit 32 may decompose each of the plural video images into four sub-band images including an LL image, an HL image, an LH image, and an HH image by performing discrete wavelet transform.

Preferably, the low-frequency video image includes a sub-band LL image, a sub-band HL image, and a sub-band LH image, and the high-frequency video image includes a sub-band HH image.

In another embodiment, the wavelet transform unit 32 may perform discrete wavelet transform with two or more decomposition levels, wherein the high-frequency video image may include a sub-band HHHH image.

The wavelet transform unit 32 may include a first wavelet transform unit 32b performing discrete wavelet transform on an n/2th frame, that is, a middle frame among the n consecutive frames, to decompose the n/2th frame into four sub-band images, that is, a sub-band LL image, a sub-band HL image, and a sub-band LH image, and a sub-band HH image and a second wavelet transform unit 32a or 32c performing discrete wavelet transform on the other frames.

The high-frequency video image summation unit 34b may generate a noise-attenuated high-frequency video image based on the high-frequency video images. Specifically, the high-frequency video image summation unit 34b may obtain a noise-attenuated sub-band HH image by summing and averaging the sub-band HH images obtained from the original 2D video composed of the n frames to cancel out noise in the sub-band HH image.

The inverse discrete wavelet transform unit 39 may generate a denoised video image by synthesizing the noise-attenuated high-frequency video image and the low-frequency video image obtained from any one of the plural video images.

Preferably, the inverse discrete wavelet transform unit 39 synthesizes the noise-attenuated high-frequency video image and the low-frequency video image obtained from a middle video image among the plural video images to generate the denoised video image.

In addition, the image signal reception sensor unit 30 of FIG. 1 or FIG. 2 may include any one selected from the group of an image sensor provided with a filter for receiving only an image in a specific frequency band, a fluorescent image sensor, an infrared image sensor, and an ultrasound array sensor and ultrasound probe sensor generating an ultrasound image, an antenna for obtaining a magnetic resonance imaging (MRI) image by computerized imaging of unique high frequency emitted from atomic nuclei due to magnetic resonance, and an X-ray detector for obtaining an X-ray image and a computer tomography (CT) image. Preferably, the image signal reception sensor unit includes a sensor that receives measured medical image signals from the body of a patient or receives measured image data from a subject.

In addition, the noise removal apparatus of FIG. 1 or FIG. 2 may further include: a silence detector determining the presence of an input signal from the image signal reception sensor unit 30; a threshold generation unit 37 generating a threshold for distinguishing noise in the sub-band HH image from actual image data; and an HH thresholder 38 regarding a pixel in the sub-band HH image having a value smaller than the generated threshold as a noise pixel and interpolating the pixel using neighboring pixels without interpolation of a pixel in the sub-band HH image having a value greater than the generated threshold to generate a noise-free sub-band HH image. Hereinafter, the HH thresholder 38 is also referred to as a "threshold determination unit".

The silence detector 40 may determine the presence or absence of an input signal from the image signal reception sensor unit 30.

Preferably, interpolation of the noise pixel by the HH Thresholder 38 is performed by any one selected from the group of nearest neighbor interpolation, bilinear interpolation, and bicubic interpolation.

The threshold generation unit 37 may generate a threshold for distinguishing actual image data from noise in the noise-attenuated high-frequency image or the noise-attenuated high-frequency video image obtained by the high-frequency image summation unit 34a or the high-frequency video image summation unit 34b when the silence detector 40 detects the absence of the input signal. The threshold generation unit 37 may generate the threshold such that an average power of the image obtained by the high-frequency image summation unit 34a or the high-frequency video image summation unit 34b is minimized or is close to the DC value (average value) of the sub-band LL image when there is no input signal from the video signal reception sensor unit 30.

The threshold determination unit 38 may remove noise from the noise-attenuated high-frequency image or the noise-attenuated high-frequency video image by comparing the generated threshold with a pixel value in the noise-attenuated high-frequency image or the noise-attenuated high-frequency video image.

In addition, in order to remove speckle noise, the noise removal apparatus of FIG. 1 or FIG. 2 may further include: a log-transform unit 33 transforming the sub-band HH image into logarithmic form; and an exponent-transform unit 36 transforming the noise-attenuated sub-band HH image obtained by the high-frequency image summation unit 34a or the high-frequency video image summation unit 34a into exponential form. Hereinafter, the log-transform unit 33 is also referred to as a "logarithmic transform unit", and the exponent-transform unit 36 is also referred to as an "exponential transform unit".

The logarithmic transform unit 33 may transform the high-frequency image or each of the high-frequency video images obtained by discrete wavelet transform into logarithmic form. The logarithmic transform unit 33 may logarithmically transform the sub-band HH images to remove speckle noise. The exponential transform unit 36 may transform the noise-attenuated high-frequency image generated by the high-frequency image summation unit 34a or the noise-attenuated high-frequency video image generated by the high-frequency video image summation unit 34b into exponential form. The exponential transform unit 36 may inversely transform the logarithmically transformed sub-band HH image into the original form thereof.

The logarithmic transform unit 33 and the exponential transform unit 36 may be activated or deactivated by a speckle noise removal command unit 42 determining whether to remove speckle noise.

Speckle noise is a general type of multiplicative noise. Thus, the speckle noise removal command unit 42 may be a multiplicative noise removal command unit. The multiplicative noise removal command unit may control activation of the logarithmic transform unit and the exponential transform unit.

The noise removal apparatus according to the present invention may further include the speckle noise removal command unit 42 determining whether to remove speckle noise, a logarithmic transform selection switch 46a, and an exponential transform selection switch 46b.

The logarithmic transform selection switch 46a and the exponential transform selection switch 46b may be activated or deactivated by the speckle noise removal command unit 42. When multiplicative noise such as speckle noise needs to be removed, the speckle noise removal command unit 42 opens the logarithmic transform selection switch 46a and the exponential transform selection switch 46b to activate the logarithmic transform unit 33 and the exponential transform unit 36. Here, the speckle noise, which has multiplicative characteristics, is converted into additive noise by logarithmic transform using the logarithmic transform unit 33. Accordingly, the summing and averaging process by the high-frequency image summation unit 34a or the high-frequency video image summation unit 34b can reduce the speckle noise by virtue of temporal averaging effects on the noise component while preserving actual image data.

When additive noise such as Gaussian noise, rather than speckle noise, needs to be removed, the speckle noise removal command unit 42 closes the logarithmic transform selection switch 46a and the exponential transform selection switch 46b to deactivate the logarithmic transform unit 33 and the exponential transform unit 36 to skip logarithmic transform and exponential transform. In this case, the summing and averaging process by the high-frequency image summation unit 34a or the high-frequency video image summation unit 34b can reduce the additive noise by virtue of temporal averaging effects on the noise component while preserving actual image data.

In addition, referring to FIG. 1 and FIG. 2, a heart pulse sensor (ECG sensor) 45 may be further provided to allow the image signal reception sensor unit 30 to receive a medical image signal or a video composed of plural consecutive frames synchronized with a heart pulse signal. That is, the noise removal apparatus according to the present invention may further include the heart pulse sensor 45.

An image signal received by the image signal reception sensor unit 30 may be synchronized with a heart pulse signal measured by the heart pulse sensor 45. That is, the image signal reception sensor unit 30 may receive an image signal or a video synchronized with the heart pulse signal.

An electrocardiogram (ECG) signal measured by the heart rate sensor 45 to ascertain movement of the heart shows a regular P wave, QRS complex, and T wave at each heartbeat. Preferably, synchronization of the medical image signal with the heart pulse signal is based on a peak value of the QRS complex in the ECG signal.

In the embodiment of FIG. 2, images in the original video composed of plural consecutive frames are preferably the same as one another. In practice, however, there is a difference between the frames constituting the original video. Moreover, even when an ultrasound device remains unmoved in an affected area of a patient, the frames are not exactly the same as one another due to hand tremor of a doctor handling the ultrasound device, a slight movement of the body of the patient, and the heartbeat of the patient. Therefore, it is very difficult to obtain the noise-attenuated high-frequency image simply by summing and averaging high-frequency images obtained from the original video composed of the plural consecutive frames. In order to maximize the temporal averaging effects, that is, effects of cancelling out noise in the high-frequency video image by summing and averaging the high-frequency images, the frames in the original video need to be identical to one another except for the noise component.

In order to solve such a problem, the noise removal apparatus of FIG. 2 may further include an image aligner 50 performing registration, matching or alignment between images in the original 2D video composed of n consecutive frames, received from the image signal reception sensor unit 30.

The image aligner 50 performs registration between the received video images. Preferably, the image aligner 50 performs semantic segmentation-based image registration, control point mapping-based image registration, or wavelet frame-based image registration.

In the present invention, a fixed image used as a reference for correcting misalignment between images is referred to as a "reference image", and an image to be matched is referred to as a "matching image".

Herein, the image registration may be classified into elastic registration (non-rigid transformation) and linear transformation (rigid transformation), such as translation, rotation, scaling, and affine transformation according to a transformation relationship between the reference image and the matching image.

In another embodiment, the image registration may be performed by intensity-based image registration or feature-based image registration. Intensity-based image registration is a technique of matching images by comparing the entire intensity (for example, darkness intensity) pattern between the images. Feature-based image registration is a technique of matching images using selected pixels, such as a feature point, that is, a technique of finding corresponding feature points in two or more images, such as point, line, border, or edge components, followed by matching the corresponding feature points to one another. An example of the feature-based image registration may include control point mapping in which the correspondence between several corresponding feature points in two images is ascertained to determine a geometric transformation relation between the two images, followed by calculation of the correspondence between other corresponding points in the two images based on the determined geometric transformation relation to match the two images.

In the present invention, the feature-based image registration preferably uses a corner point. Preferably, the corner point includes pixels which can be easily identified even with change of the shape, size, or position of an object and locations of which can be easily detected in an image even with change of illumination of a camera. Specifically, the corner point may be a pixel that causes significant changes to an image in all directions (in vertical, horizontal and diagonal directions) when a small predetermined window movable vertically and laterally is shifted on the image while gradually scanning the image. Examples of an algorithm for extracting the corner point may include Harris corner detection, scale-invariant feature transform (SIFT), speeded-up robust features (SURF) and features from accelerated segment test (FAST).

In a further embodiment, the image registration may be performed by a spatial domain method or a frequency domain method. The spatial domain method is a method of detecting a point in a temporal space, at which the cross-correlation coefficient between the reference image and the matching image reaches a maximum value thereof, based on the pixel intensity pattern or feature of the images, finding a parameter required for geometric transformation between the two images using the point, and selecting the parameter as a relative motion vector between the two images. In addition, the frequency domain method is a method of performing Fourier transform on the reference image and the matching image, detecting a point in a Fourier space, at which the phase cross-correlation coefficient between the two images reaches a maximum value thereof, finding a parameter required for geometric transformation between the two images using the point, and selecting the parameter as a relative motion vector between the two images.

In yet another embodiment, the image registration may be performed by semantic segmentation-based image registration.

Semantic segmentation may be performed using an artificial neural network that detects a location of an object corresponding to a specific class in a given image by object classification on a pixel-by-pixel basis and separates the object from the other objects, provided that the object is present in the image. The artificial neural network is a neural network that can be trained by deep learning, and may include at least one selected from the group of a convolution layer, a pooling layer, an ReLu layer, a transpose convolution layer, an unpooling layer, a 1×1 convolutional layer, a skip connection, a global average pooling (GAP) layer, a fully connected layer, and combinations thereof. The artificial neural network may be an artificial neural network which further includes an operation unit for batch normalization upstream of the ReLu layer. Preferably, the artificial neural network is a convolutional neural network (CNN) or a recurrent neural network (RNN).

In the present invention, the semantic segmentation-based image registration may use a semantic segmented reference image and a semantic segmented matching image each obtained by labelling different organs in a medical image with different colors. Here, registration between the semantic segmented reference image and the semantic segmented matching image may be performed by detecting a point in a temporal space, at which the cross-correlation coefficient between the two images reaches a maximum value thereof, finding a parameter required for geometric transformation between the two images using the point, and selecting the parameter as a relative motion vector between the two images.

In yet another embodiment, the image registration may be performed by wavelet frame or redundant (over-complete) wavelet-based image registration. In wavelet frame or redundant (over-complete) wavelet-based image registration, wavelet frame transform is performed on the reference image and the matching image, followed by finding a cross-correlation coefficient between corresponding sub-band frame images of the two images using at least one selected from the group of the sub-band HL frame image, the sub-band LH frame image, and the sub-band HH frame image, and then a parameter required for geometric transformation between the two images is found using a point at which the cross-correlation coefficient between the corresponding sub-band frame images of the two images reaches a maximum value thereof, followed by selecting the parameter as a relative motion vector between the two images. Since subsampling by a factor of ½ is not performed in the wavelet frame or redundant wavelet transform, the size of the sub-band frame images does not change before and after transform. In addition, since the sub-band HL frame image has a highlighted horizontal edge component and the sub-band LH frame image has a highlighted vertical edge component, the sub-band HL frame image and the sub-band LH frame image can sufficiently provide edge feature points that can be conveniently used for image registration.

In another embodiment, in the wavelet frame or redundant (over-complete) wavelet-based image registration, overlapping pixels between the sub-band HL frame image, the sub-band LH frame image, and the sub-band HH frame image may be selected as the corner point for image registration. The overlapping pixels may be pixels having a value greater than a corner point determination threshold, wherein the pixels are found by performing pixel-by-pixel multiplication between the sub-band HL frame image, the sub-band LH frame image, and the sub-band HH frame image, followed by application of the corner point determination threshold on a pixel-by-pixel basis. Alternatively, the overlapping pixels may be found by applying a corner point determination threshold to each of the sub-band HL frame image, the sub-band LH frame image, and the sub-band HH frame image on a pixel-by-pixel basis, followed by performing pixel-by-pixel multiplication on an image composed of pixels having a greater value than the corner point determination threshold.

In the present invention, a small image obtained by collecting pixels around the feature point is referred to as a "patch".

In the present invention, the cross-correlation coefficient is preferably found by comparing the patch between the reference image and the matching image. The image aligner 50 according to the present invention may perform image registration by control point mapping in which a transformation relation between the two images is determined by ascertaining a correspondence between corresponding feature points based on patches having high similarity, followed by calculation of a correspondence between other corresponding points in the images based on the determined transformation relation.

Preferably, the cross-correlation coefficient may be any one selected from the group of sum of squared difference (SSD), sum of absolute difference (SAD), and normalized cross correlation (NCC).

In addition, the noise removal apparatus of FIG. 2 may further include an outlier detection unit 52 discarding a frame (matching image) that contains a large number of feature points, at which a motion vector required for image registration has an unusually large value.

The outlier detection unit 52 may eliminate a matching image that is significantly misaligned with the reference image upon image registration by the image aligner. Specifically, the outlier detection unit 52 may detect a matching image containing feature points at which a motion vector between the reference image and the matching image exceeds a predetermined value to exclude the detected matching image from the process of summing and averaging the high-frequency video images. That is, the outlier image (outlier matching image) detected by the outlier detection unit 52 cannot participate in the summing and averaging process by the high-frequency video image summation unit 34*b*.

In the present invention, it is desirable that the outlier detection unit 52 discard a matching image having a feature point at which a motion vector between the reference image and the matching image has a length of 100 pixels or more in each of the horizontal and vertical directions thereof.

Figure 3:
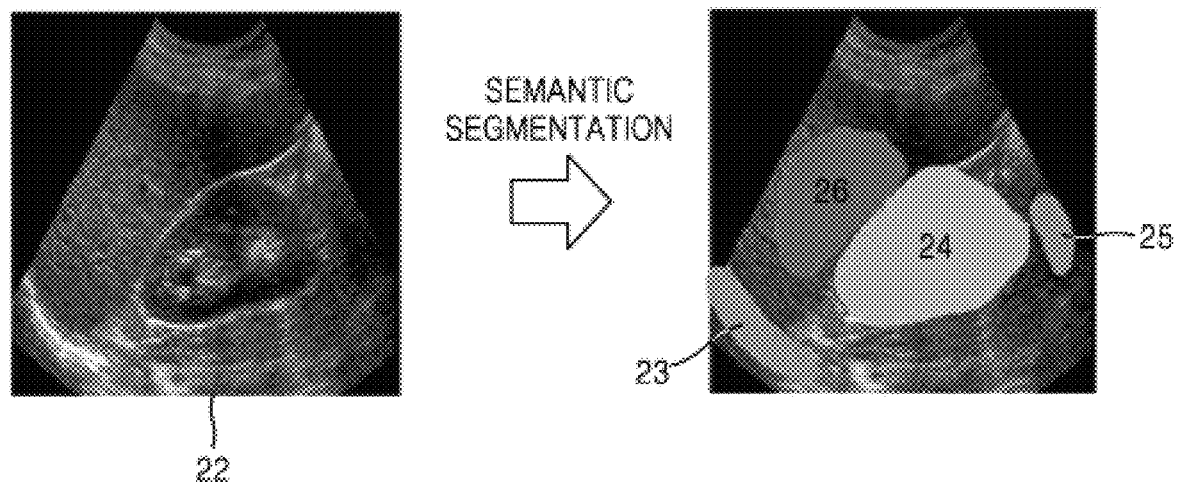
FIG. 3 shows an embodiment in which semantic segmentation is performed on an ultrasound image to perform semantic segmentation-based image registration.

FIG. 3 shows an example in which semantic segmentation is performed on an ultrasound image 22 in a parasagittal scan plane for semantic segmentation-based image registration of the ultrasound image 22. Here, the ultrasound image 22 is an ultrasound image obtained by placing an ultrasound probe sensor in a parasagittal scan plan with respect to an affected area.

In FIG. 3, reference numeral 26 denotes a liver, reference numeral 25 denotes a spleen, reference numeral 24 denotes a kidney, and reference numeral 23 denotes a diaphragm.

In the present invention, semantic segmentation-based image registration is performed based on a color map of organs which is configured by assigning different colors to different organs in the reference image. In FIG. 3, the color map is configured by assigning green to the liver, yellow to the kidney, blue to the spleen, and orange to the diaphragm.

Figure 4:
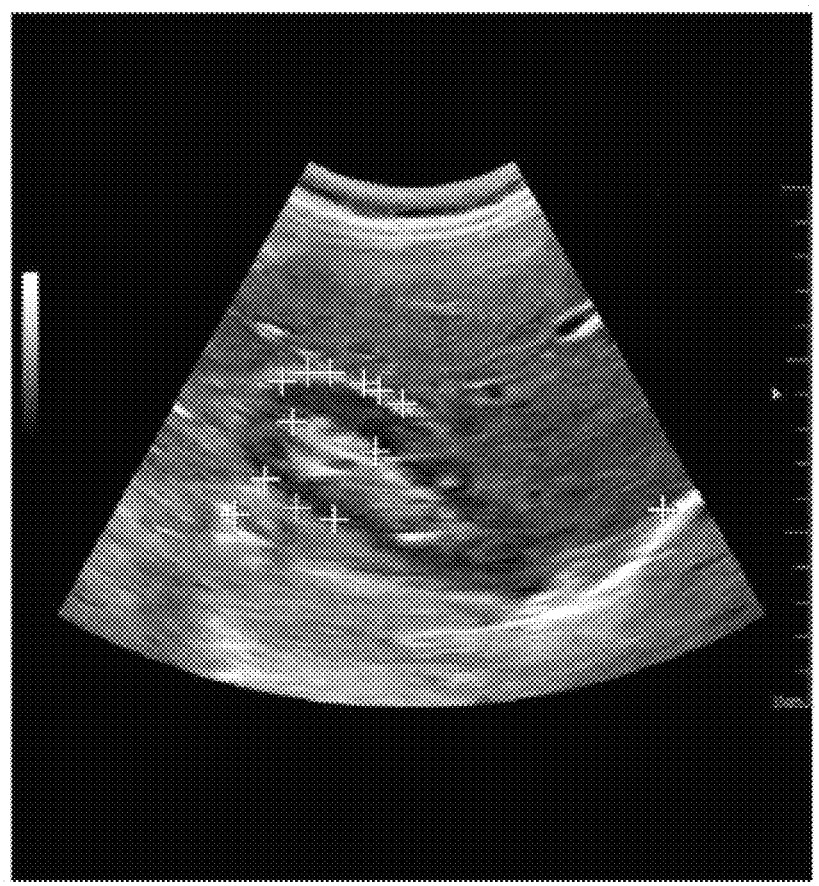
FIG. 4 shows an embodiment in which corner points are displayed in an ultrasound image to perform feature-based image registration.

FIG. 4 shows exemplary corner points displayed on an ultrasound image in a parasagittal scan plane for feature-based image registration. The corner points (indicated by '+' in the drawing) are used in control point mapping-based image registration.

Figure 5:
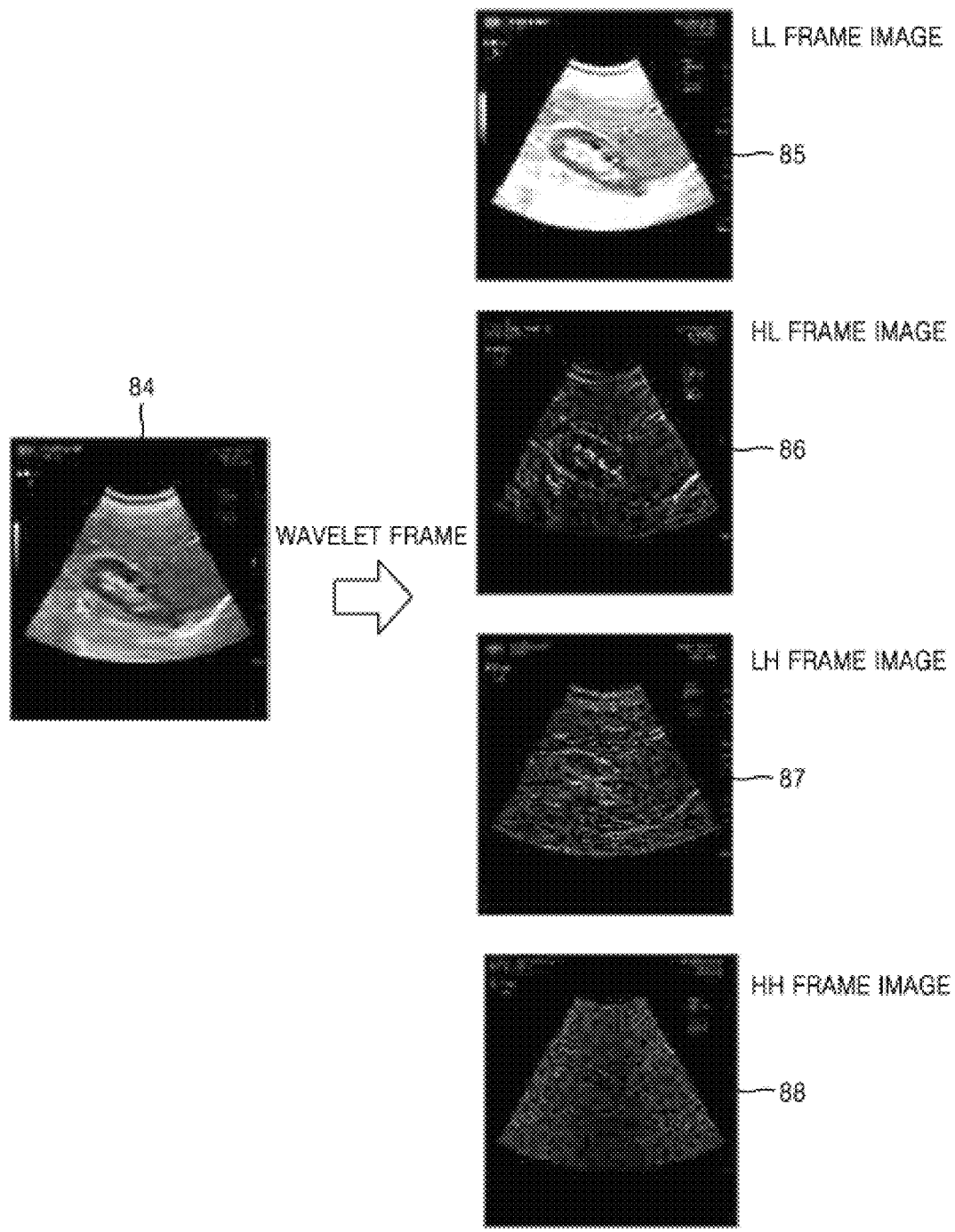
FIG. 5 shows exemplary sub-band frame images obtained by wavelet frame transform of an ultrasound image to perform wavelet frame-based image registration.

FIG. 5 shows a sub-band LL frame image 85, a sub-band HL frame image 86, a sub-band LH frame image 87, and a sub-band HH frame image 88 obtained by wavelet frame transform of an ultrasound image 84 for wavelet frame or redundant (over-complete) wavelet-based image registration.

In the present invention, it is desirable to perform image registration using the sub-band HL image 86 and the sub-band LH image 87, which are abundant in feature points, among the sub-band frame images.

Figure 6:
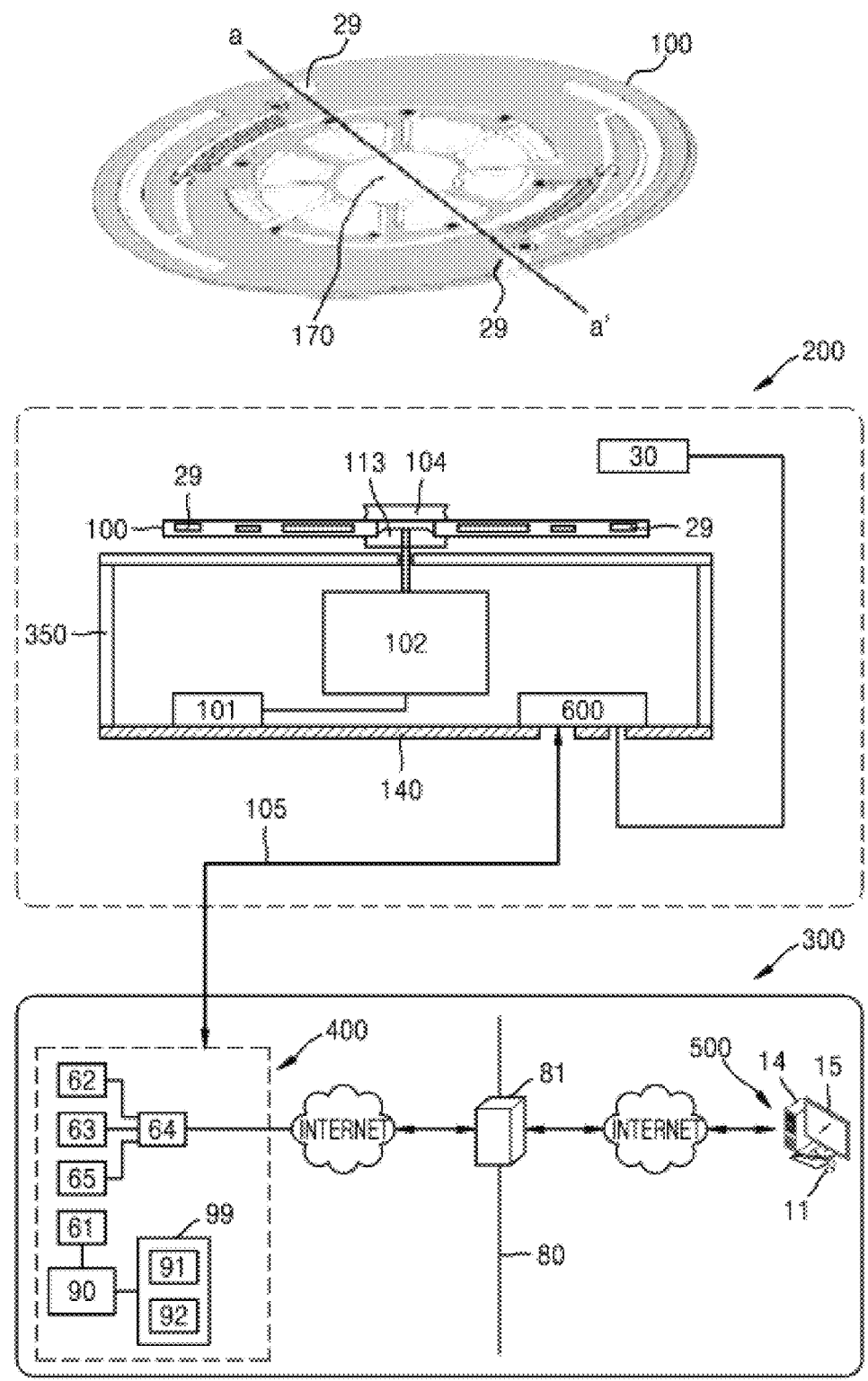
FIG. 6 is a schematic diagram of a remote medical diagnosis system according to one embodiment of the present invention, which is associated with a bioanalyzer driving a lab-on-a-disc and a noise removal apparatus for removing noise from image data obtained by the bioanalyzer, wherein the remote medical diagnosis system automatically analyzes a result of bioreaction to perform diagnosis and provides a user with a consultation service with a medical expert.

FIG. 6 is a diagram of a remote medical diagnosis system 300 according to one embodiment of the present invention, wherein the remote medical diagnosis system is associated with the noise removal apparatus 600 of FIG. 1 receiving image data from a bioanalyzer 200 as the image signal, the remote medical diagnosis system automatically analyzing a result of bioreaction to perform diagnosis and providing a user with a consultation service with a medical expert.

The bioanalyzer 200 drives a bio-disc or lab-on-a-disc 100 performing a biological, chemical or biochemical reaction and includes a fluorescence image sensor or image sensor 30 capturing a result of bioreaction on the bio-disc 100 as the image data and the noise removal apparatus 600 of FIG. 1 removing noise from the captured image data.

In addition, the bioanalyzer 200 further includes a turntable 113 allowing the lab-on-a-disc 100 to be placed thereon, a motor 102 rotating the lab-on-a-disc 100 on the turntable 113, and a central controller 101. Reference numeral 350 denotes a body supporting the bioanalyzer 200. The bioanalyzer 200A is provide at a bottom side thereof with a circuit board 140 jointly fastened to the body 350, such that the central controller 101 and the noise removal apparatus 600 are placed on the circuit board 140. The central controller 101 controls the motor 102 to rotate or stop the lab-on-a-disc 100 and controls the fluorescence image sensor or image sensor 30. Reference numeral 104 denotes a means of pressing the disc 100 loaded in a cavity 170 of the disc, wherein the means presses the disc 100 by magnetic attraction to the turntable 113 and is preferably designed to be movable vertically and to be rotatable under no-load conditions.

The remote medical diagnosis system 300 includes a user terminal 400, a remote diagnosis server 81, and a medical expert terminal 500. In addition, the remote medical diagnostic system 300 may include the bioanalyzer 200.

The user terminal 400 is connected to the apparatus for removing noise 600 via a communication interface and may provide a user with a consultation service with a medical expert using a denoised image. The remote diagnosis server 81 may transmit data between the user terminal 400 and the medical expert terminal 500. The medical expert terminal 500 may receive image data from the remote diagnosis server 81 and provide a user with a consultation service with a medical expert.

The user terminal 400 includes a camera 61 monitoring use of the bioanalyzer 200, a first authentication unit 62 authenticating a product ID of the lab-on-a-disc 100, a recording unit 63 storing denoised image data obtained by the noise removal apparatus 600, an Internet connector 64 transmitting the image data and the product ID of the lab-on-a-disc 100 to the remote diagnosis server 81 via a communication network 80 and providing a communication channel for a remote consultation service, and a first consultation service unit 65 providing a consultation service with a medical expert.

In addition, the user terminal 400 further includes an artificial neural network 90 residing as software therein and trained on an image database accumulated by the bioanalyzer 200 by deep learning, a guide unit 91 residing as software therein and guiding or instructing how to use the bioanalyzer 200, and a diagnosis unit 92 outputting a diagnostic result obtained by automatic analysis of the image data obtained by the noise removal apparatus 600 using the deep learning-trained artificial neural network 90. Hereinafter, the guide unit and the diagnosis unit will be collectively referred to as a "virtual doctor" 99.

Further, the user terminal 400 is connected to the noise removal apparatus 600 via the communication interface 105.

In addition, FIG. 6 shows a sectional view of the lab-on-a-disc 100 loaded on the bioanalyzer 200, taken along line a-a', wherein the lab-on-a-disc 100 includes a DNA amplification chamber 29 performing DNA amplification.

As described above, the bioanalyzer 200 may include the bio-disc performing a biological, chemical or biochemical reaction, the central controller driving the bio-disc, the noise removal apparatus 600 according to the present invention, and the image sensor capturing a result of bioreaction performed on the bio-disc as the image data.

The virtual doctor 99 may quantitatively or qualitatively analyze a DNA amplification product from the DNA amplification chamber 29.

The medical expert terminal 500 includes a receiver receiving the image data via the communication network 80 and a second consultation service unit providing a user with a consultation service with a medical expert.

Figure 7:
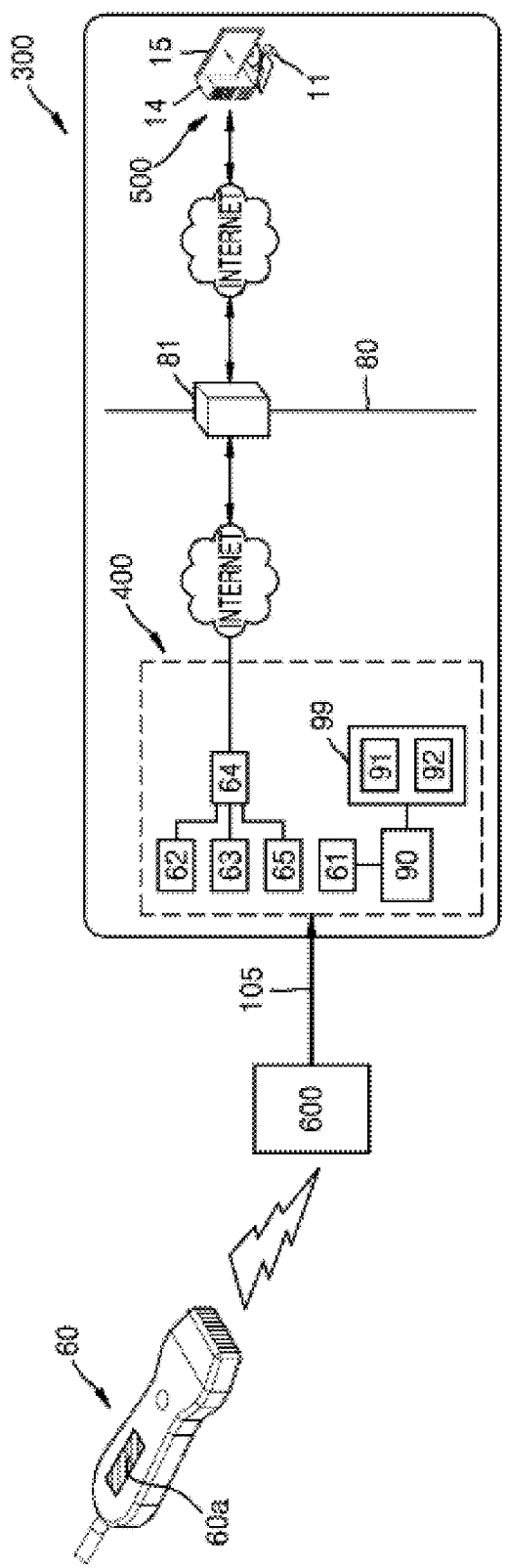
FIG. 7 is a schematic diagram of a remote medical diagnosis system according to another embodiment of the present invention, which is associated with a noise removal apparatus for removing noise from medical image data on a patient obtained by a medical device, wherein the remote medical diagnosis system automatically analyzes the medical image data on the patient to perform diagnosis and provides a user with a consultation service with a medical expert.

FIG. 7 is a diagram of a remote medical diagnosis system 300 according to another embodiment of the present invention, wherein the remote medical diagnosis system is associated with the noise removal apparatus 600 of FIG. 1 or FIG. 2 receiving medical image data on a patient obtained by any one medical device selected from the group of X-ray, ultrasound, CT, and MRI devices, the remote medical diagnosis system 300 automatically analyzing the medical image data on the patient to perform diagnosis and providing a user with a consultation service with a medical expert.

The medical device 60 includes a wireless transmitter 60a wirelessly transmitting the measured medical image data on the patient.

The noise removal apparatus 600 removes noise from the medical image data on the patient received from the wireless transmitter 60a.

A user terminal of the remote medical diagnosis system 300 includes a camera monitoring use of the medical device 60, a second authentication unit 62 wirelessly authenticating a product ID of the medical device 60, a recording unit 63 storing the medical image data on the patient obtained by the medical device 60, an Internet connector 64 transmitting the medical image data and the product ID of the medical device to a remote diagnosis server 81 via a communication network 80 and providing a communication channel for a remote consultation service, and a third consultation service unit 65 providing a consultation service with a medical expert. The user terminal 400 is connected to the noise removal apparatus 600 via a communication interface 105. Here, the second authentication unit 62 may perform a function corresponding to that of the first authentication unit 62. In addition, the third consultation service unit 65 may perform a function corresponding to that of the first consultation service unit 65.

In addition, the user terminal 400 further includes an artificial neural network 90 residing as software therein and trained on an image database accumulated by the medical device 60 by deep learning, a guide unit 91 residing as software therein and guiding or instructing how to use the medical device 60, and a diagnosis unit 92 outputting a diagnostic result obtained by automatic analysis of the medical image data obtained by the medical device 60 using the deep learning-trained artificial neural network 90.

The guide unit 91 serves to guide or instruct a user on how to use the medical device 60 based on results of monitoring use of the medical device 60 in real time using the camera 61.

A medical expert terminal 500 of the remote medical diagnosis system 300 includes a receiver receiving the medical image data via the communication network 80 and a fourth consultation service unit providing a user with a consultation service with a medical expert. Here, the fourth consultation service unit may perform a function corresponding to that of the second consultation service unit.

The medical expert terminal 500 may further include a camera 14, a microphone 15, and a mouse 11.

A remote medical diagnosis method using the remote medical diagnosis system according to one embodiment of the present invention includes the steps of: removing, by the noise removal apparatus, noise from image data on the lab-on-a-disc or medical image data on a patient obtained by the medical device; training an artificial neural network on a database by deep learning; outputting, by the virtual doctor in the user terminal, a diagnostic result obtained by automatic analysis of the denoised image data or the denoised medical image data using the deep learning-trained artificial neural network; and transmitting the denoised image data or the denoised medical image data on the patient to the remote diagnosis server via the communication network; and performing a remote consultation service with a medical expert.

The remote medical diagnosis method according to the present invention may be realized in the form of program instructions which can be implemented through various computer components, and may be recorded in a computer-readable storage medium. The computer-readable storage medium may include program instructions, a data file, a data structure, and the like either alone or in combination thereof. The program instructions recorded in the computer-readable storage medium may be any program instructions particularly designed and structured for the present invention or known to those skilled in the field of computer software. Examples of the computer-readable storage medium include magnetic recording media, such as hard disks, floppy disks and magnetic tapes, optical data storage media, such as CD-ROMs and DVD-ROMs, magneto-optical media such as floptical disks, and hardware devices, such as read-only memories (ROMs), random-access memories (RAMs), and flash memories, which are particularly structured to store and implement the program instructions. Examples of the program instructions include not only assembly language code formatted by a compiler but also high-level language code which can be implemented by a computer using an interpreter. The hardware device described above may be configured to operate as one or more software modules to perform operations of the present invention, and vice versa.

Although some embodiments have been described herein, it should be understood that these embodiments are provided for illustration and that various modifications, changes, alterations, and equivalent embodiments can be made by those skilled in the art without departing from the spirit and scope of the invention. Therefore, the embodiments are not to be construed in any way as limiting the present invention. For example, each component described as a single type may be implemented in a distributed manner, and, similarly, components described as distributed may be implemented in a combined form.

The scope of the present application should be defined by the appended claims and equivalents thereof rather than by the detailed description, and all changes or modifications derived from the spirit and scope of the claims and equivalents thereof should be construed as within the scope of the present invention.

LIST OF REFERENCE NUMERALS

600: Noise removal apparatus
30: Image signal reception sensor unit
32: Wavelet transform unit
33: Log-transform unit
34a: High-frequency image summation unit
34b: High-frequency video image summation unit
35: Noise generator
36: Exponent-transform unit
37: Threshold generation unit
38: HH thresholder
39: Inverse discrete wavelet transform unit
40: Silence detector
42: Speckle noise removal command unit
50: Image aligner
52: Outlier detection unit

What is claimed is:

1. A noise removal apparatus comprising:
an image signal reception sensor configured to receive a measured image signal;
a wavelet transformer including a low pass filter and a high pass filter, the wavelet transformer configured to perform a discrete wavelet transform on the image signal received from the image signal reception sensor via the low pass filter and the high pass filter to divide the image signal into a low-frequency image composed of a low-frequency component and a high-frequency image composed of a high-frequency component;
a noise generator configured to generate plural noise images containing noise similar to a noise component in the high-frequency image;
a logarithmic transformer configured to receive the high-frequency image from the wavelet transformer, and transform the high-frequency image into a logarithmic form;
a noise-attenuated, high-frequency image summation unit configured to receive the high-frequency image and the plural noise images generated by the noise generator, and sum and average the high-frequency image and the plural noise images to generate a noise-attenuated, high-frequency image;
an exponential transformer configured to receive the noise-attenuated, high-frequency image from the noise-attenuated, high-frequency image summation unit, and inversely transform the noise-attenuated, high-frequency image into an original form;
a thresholder configured to receive the noise-attenuated, high-frequency image, identify a pixel in the noise-attenuated, high-frequency image having a pixel value smaller than a threshold as a noise pixel, and interpolate the noise pixel using neighboring pixels without interpolation of a pixel in the noise-attenuated, high-frequency image having a pixel value greater than the threshold, to generate a noise-free, high-frequency image; and
an inverse discrete wavelet transformer configured to receive the low-frequency image and the noise-free, high-frequency image and synthesize the low-frequency image and the noise-free, high-frequency image to generate a denoised image.

2. A noise removal apparatus comprising:
an image signal reception sensor configured to receive a measured video;
a wavelet transformer including a low pass filter and a high pass filter, the wavelet transformer configured to perform a discrete wavelet transform on images in the video received from the image signal reception sensor and composed of plural consecutive frames, via the low pass filter and the high pass filter to divide each of the images into a low-frequency video image composed of a low-frequency component and a high-frequency video image composed of a high-frequency component;
a logarithmic transformer configured to receive the high-frequency video images from the wavelet transformer and transform each of the high-frequency video images into a logarithmic form;
a noise-attenuated, high-frequency video image summation unit configured to receive the high-frequency video images, and sum and average the high-frequency video images obtained from the video composed of the plural consecutive frames to generate a noise-attenuated, high-frequency video image;
an exponential transformer configured to receive the noise-attenuated, high-frequency video image from the noise-attenuated, high-frequency video image summation unit, and inversely transform the noise-attenuated, high-frequency video image into an original form;
a thresholder configured to receive the noise-attenuated, high-frequency video image, identify a pixel in the noise-attenuated, high-frequency video image having a pixel value smaller than a threshold as a noise pixel, and interpolate the noise pixel using neighboring pixels without interpolation of a pixel in the noise-attenuated, high-frequency video image having a pixel value greater than the threshold, to generate a noise-free, high-frequency video image; and
an inverse discrete wavelet transformer configured to receive the low-frequency video images and the noise-free, high-frequency video image, and synthesize the noise-free, high-frequency video image with a low-frequency image corresponding to a middle frame among the low-frequency video images to generate a denoised image.

3. The noise removal apparatus according to claim 1, wherein the low-frequency image comprises a sub-band Low-Low (LL) image, a sub-band High-Low (HL) image, and a sub-band Low-High (LH) image, and the high-frequency image comprises a sub-band High-High (HH) image.

4. The noise removal apparatus according to claim 1, wherein the high-frequency image comprises a high-frequency sub-band image obtained by performing discrete wavelet transform or discrete wavelet packet transform with two or more decomposition levels.

5. The noise removal apparatus according to claim 3, further comprising:
a silence detector configured to determine the presence of an input signal from the image signal reception sensor; and
a threshold generator configured to generate the threshold for distinguishing noise in the sub-band HH image from actual image data; and
wherein the identified pixel is a pixel in the sub-band HH image.

6. The noise removal apparatus according to claim 5, wherein:
the logarithmic transformer is configured to logarithmically transform the sub-band HH images to remove speckle noise; and
the exponential transformer is configured to inversely transform the logarithmically transformed sub-band HH image back into an original form thereof.

7. The noise removal apparatus according to claim 6, further comprising:
a speckle noise removal controller configured to determine whether to remove speckle noise;
a first switch associated with the logarithmic transformer; and
a second switch associated with the exponential transformer,
wherein the speckle noise removal controller is configured to control the first switch and the second switch to activate or deactivate the logarithmic transformer or the exponential transformer.

8. The noise removal apparatus according to claim 1, further comprising:
a heart pulse sensor configured to measure a heart pulse signal,
wherein the image signal reception sensor is configured to receive an image signal synchronized with the heart pulse signal.

9. The noise removal apparatus according to claim 2, further comprising:
an image aligner configured to perform registration or alignment between the frames of the video; and
an outlier detector configured to detect a matching image containing feature points at which a motion vector between a reference image and the matching image exceeds a predetermined value upon registration between the frames by the image aligner to exclude the matching image from the summing and averaging performed by the noise-attenuated, high-frequency video image summation unit.

10. The noise removal apparatus according to claim 9, wherein the image aligner configured to perform alignment or registration between two neighboring frames using semantic segmentation-based image registration, control point mapping-based image registration, or wavelet frame-based image matching.

11. A remote medical diagnosis system comprising:
a bioanalyzer including the noise removal apparatus according to claim 1; and
a user terminal connected to the noise removal apparatus via a communication interface.

12. A remote medical diagnosis system comprising:
the noise removal apparatus according to claim 1;
a medical device comprising a transmitter configured to transmit medical image data to the noise removal apparatus; and
a user terminal connected to the noise removal apparatus via a communication interface.

13. A remote medical diagnosis method comprising the steps of:
removing, by the noise removal apparatus according to claim 1, noise from medical image data on a patient obtained by a medical device;
training an artificial neural network on a database accumulated by the medical device by deep learning;
outputting a diagnostic result obtained by automatic analysis of a denoised medical image data obtained by the noise removal apparatus using a deep learning-trained artificial neural network; and
transmitting the denoised medical image data to a remote diagnosis server via a communication network and providing a remote consultation service with a medical expert.

14. The noise removal apparatus according to claim 2, wherein the-low-frequency video image comprises a sub-band Low-Low (LL) image, a sub-band High-Low (HL) image, and a sub-band Low-High (LH) image, and the high-frequency video image comprises a sub-band High-High (HH) image.

15. The noise removal apparatus according to claim 2, wherein the high-frequency video image comprises a high-frequency sub-band image obtained by performing discrete wavelet transform or discrete wavelet packet transform with two or more decomposition levels.

16. The noise removal apparatus according to claim 14, further comprising:
a silence detector configured to determine the presence of an input signal from the image signal reception sensor; and
a threshold generator configured to generate the threshold for distinguishing noise in the sub-band HH image from actual image data; and
wherein the identified pixel is a pixel in the sub-band HH image.

17. The noise removal apparatus according to claim 16, wherein:
the logarithmic transformer is configured to logarithmically transform the sub-band HH images to remove speckle noise; and
the exponential transformer is configured to inversely transform the logarithmically transformed sub-band HH image back into an original form thereof.

18. The noise removal apparatus according to claim 17, further comprising:
a speckle noise removal controller configured to determine whether to remove speckle noise;
a first switch associated with the logarithmic transformer; and
a second switch associated with the exponential transformer,
wherein the speckle noise removal controller is configured to control the first switch and the second switch to activate or deactivate the logarithmic transformer or the exponential transformer.

19. The noise removal apparatus according to claim 2, further comprising:
a heart pulse sensor configured to measure a heart pulse signal,
wherein the image signal reception sensor is configured to receive a video synchronized with the heart pulse signal.

20. The noise removal apparatus according to claim 1, wherein the noise generator is configured to generate random numbers following a distribution having a predetermined average and variance, and generate the plural noise images based on the random numbers.

* * * * *